United States Patent [19]

Suma

[11] Patent Number: 4,654,028
[45] Date of Patent: Mar. 31, 1987

[54] INCISION OPENING EXPANSION HOLDER FOR INOSCULATION

[76] Inventor: Hisayoshi Suma, High-Lark Nishi Kyogoku 101, 64 Hamanohommachi, Nishi Kyogoku, Ukyo-ku, Kyoto, Japan

[21] Appl. No.: 823,950

[22] Filed: Jan. 29, 1986

[30] Foreign Application Priority Data

Mar. 14, 1985 [JP] Japan .................................. 60-51352

[51] Int. Cl.⁴ ............................................ A61L 17/11
[52] U.S. Cl. .................................... 604/106; 604/107; 128/303 R; 128/321; 128/341; 128/334 R; 128/345
[58] Field of Search ............... 604/104, 106, 107, 108, 604/158; 128/303 R, 341, 343, 345, 20, 7, 4, 303.15, 321, 334 R, 334 C, 335, 335.5

[56] References Cited

U.S. PATENT DOCUMENTS

| | | | |
|---|---|---|---|
| 2,137,710 | 11/1938 | Anderson | 128/321 |
| 3,858,586 | 1/1975 | Ressen | 128/4 |
| 3,934,589 | 1/1976 | Zimmer | 128/321 |
| 3,938,527 | 2/1976 | Rioux et al. | 128/321 |
| 4,174,715 | 11/1979 | Hasson | 128/321 |
| 4,222,380 | 9/1980 | Terayama | 128/4 |
| 4,249,533 | 2/1981 | Komiya | 128/321 |
| 4,393,872 | 7/1983 | Reznik et al. | 604/106 |
| 4,467,802 | 8/1984 | Maslanka | 128/321 |

*Primary Examiner*—C. Fred Rosenbaum
*Assistant Examiner*—John Ferros
*Attorney, Agent, or Firm*—Moonray Kojima

[57] ABSTRACT

An incision opening expansion holder for use surgical operation, especially for inosculation comprising an outer tube being capable of inserting into the lumen of a vein graft, an inner tube slidably inserting into the outer tube and a grip being fixed to one end of the inner tube, the inner tube has a plurality of short wires, the bases of which are fixed to the other end of the inner tube and each wire is to be energized to expand so as to hold the incision opening of the vein graft open when the holder is inserted into the lumen and also when the wires of the inner tube are projected out of the outer tube by handling the grip, so that inosculation operation can be undertaken under good visual field and surgeons can observe easily the piercing point of sewing of the vein graft.

2 Claims, 11 Drawing Figures

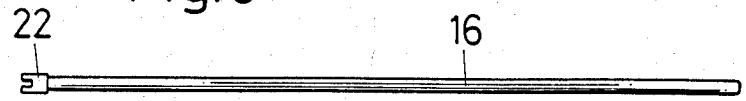
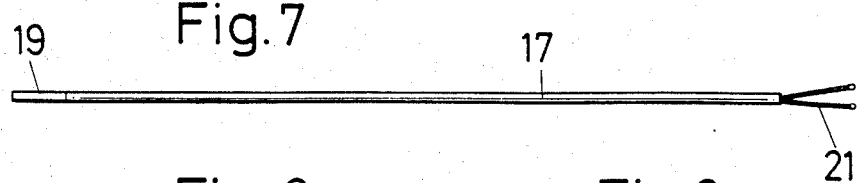
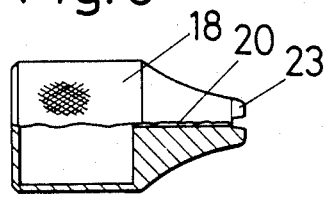 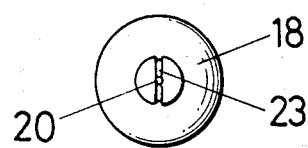
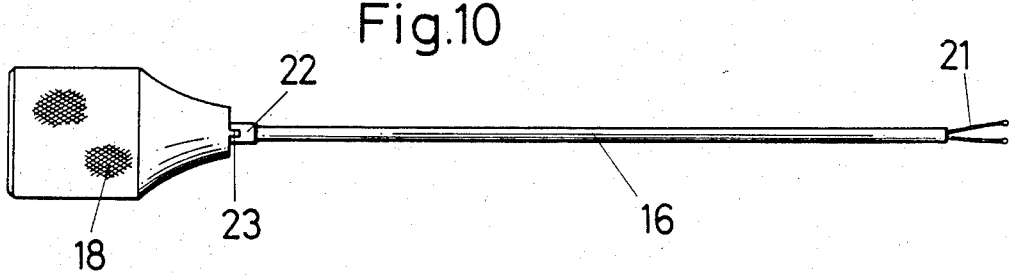
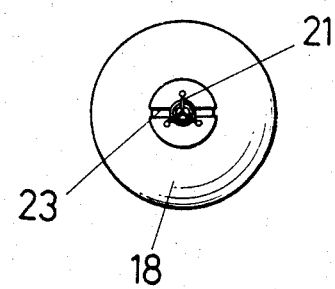

INCISION OPENING EXPANSION HOLDER FOR INOSCULATION

BACKGROUND OF THE INVENTION

This invention relates to an incision opening expansion holder for a graft of blood vessel used in surgical operation, particularly for inosculation.

Heretofore, an operation for inosculation of blood vessel has mainly relied upon handicraft of seaming by surgeons with their fingertips using tweezers, needles and thread. Only an implement called blood vessel seaming device which serves to inosculate blood vessel in longitudinal direction has been known. The implement of this type, however, cannot be used for such inosculation of blood vessel as seaming a bypass to an incision opening provided on the side wall of the blood vessel.

In such operation as providing a coronary artery bypass which inosculates the coronary arteries, using a vein graft, it is essential for keeping the inosculated opening of the graft open after the operation to make the operation under good visual field with the incision opening spread three dimensionally.

However, even though surgeon tries to open the incision opening using tweezers, it may be very difficult to hold the opening three dimensionally in stationary state so as to obtain good visual field during operation.

SUMMARY OF THE INVENTION

The primary object of the present invention is to provide an instrument which can keep an incision opening of blood vessel graft fully open and which hold the part to be inosculated three dimensionally for sufficient field of view during operation.

Another object of the invention is to provide an instrument which can be inserted into the lumen of blood vessel graft and which expands the part to be inosculated of the graft from the lumen.

Still another object of the invention is to provide some short wires fixed to the end of the inner tube which serve to hold the incision opening open to the extent of not tearing up, when the incision opening is expanded from the lumen of blood vessel graft.

Further object of the invention is to provide an instrument which has an outer tube, an inner tube slidably accomodated into the outer tube and a grip, the inner tube has a plurality of wires, the wires expand the incision opening of blood vessel graft from the lumen of the graft in three dimensions by handling the grip.

Still further object of the invention is to provide an instrument which has a round part on the end of each wires so that blood vessel graft is not injured when the incision opening is expanded from the lumen of the graft.

To attain these objects, the present invention provides an incision opening expansion holder for use the surgical operation like inosculation of blood vessel graft, comprising an outer tube which can be inserted into the lumen of blood vessel graft, an inner tube slidably inserted into the outer tube and a grip fixed to one end of the inner tube, the inner tube has a plurality of wires fixed to the end of the inner tube with their base and accomodated in the outer tube, each wires being energized to expand blood vessel graft from the lumen when released from the compression of the outer tube by handling the grip and sliding the inner tube inside of the outer tube to project the wires.

Thus, the incision opening expansion holder according to the invention having a slender outer tube, as in the case of coronary artery bypass operation using a vein piece as the graft, can be inserted into the lumen of the blood vessel and with its end positioned at the incision opening of the graft, slide the inner tube from the outer tube so that some wires project out from the outer tube and are spread to expand the incision opening larger than the diameter of the outer tube.

To spread the wires in three dimensions, the inner tube is slided inside of the outer tube by handling the grip so that the wires project out of the outer tube. Each wire curves a little in the direction of parallel with an axis of the tube for preventing from injuring the lumen of the graft.

The incision opening expansion holder for inosculation according to the invention can be easily and certainly inserted into the lumen of a graft of blood vessel of about 2 to 6 mm in diameter, and can slide the inner tube relatively in the vicinity of the incision opening by using the grip, to project out the wires. The wires projected out of the outer tube are individually energized so as to open three dimensionally and to expand the incision opening adequately. Thus, operation of accurate needling around the inosculation opening has become easy and safe. Accordingly, operation for inosculation of a side wall of vein graft to that of the artery (side-to-side inosculation) like coronary artery bypass operation, has also become easy and gives a large effect on surgical operation.

After operation, the inner tube is pulled into the outer tube and the wires are accomdated again into the outer tube.

BRIEF DESCRIPTION OF THE DRAWINGS

FIGS. 6 to 9 are exploded plan views showing another embodiment, in which FIG. 6 is a plan view of the outer tube, FIG. 7 is a plan view of the inner tube, FIG. 8 is a plan view of the grip partly sectional, and FIG. 9 is a side view of the grip.

FIG. 10 is a plan view of the assembly.

FIG. 11 is a side view of the same.

DETAILED DESCRIPTION OF PREFERRED EMBODIMENTS

EXAMPLE 1

Figure 1:
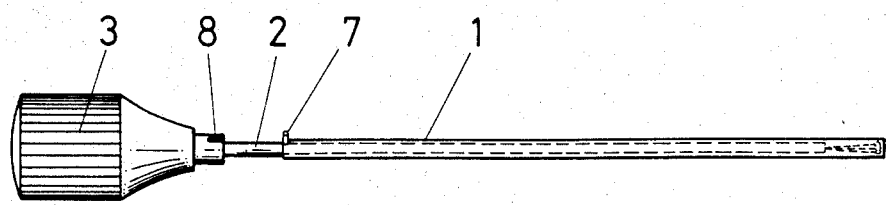
FIG. 1 is a perspective view showing the incision opening expansion holder for inosculation as a first embodiment of the invention.
Figure 2:
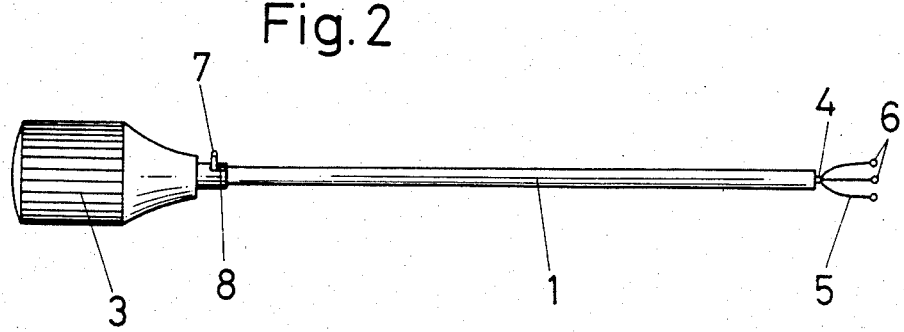
FIG. 2 is a perspective view of the same projecting out of the wires.

In FIG. 1, 1 represents an outer tube and 2 represents an inner tube. The inner tube 2 has nearly the same lengh as the outer tube and slidably inserted into the outer tube 1. The diameter of the outer tube is about 4 mm and the length is about 150 mm. A grip 3 is fixed to one end of the inner tube 2. The grip has such a size as can be caught by the palm (30 mm in diameter, 55 mm in length). A plurality of wires 5 are fixed to the other end of the inner tube. These wires 5 can be accomodated in the outer tube, and at the same time are individually energized so as to expand in three dimensions when projecting out of the outer tube. This energizing force is naturally to expand the incision opening of blood vessel graft to such a degree as facilitating the operation, and must not break the blood vessel. In order to protect from injuring the lumen of the graft, the wires are curved a little in the direction of parallel with an axis of the tube. In addition, the round part 6 attached to the end of each wire 5 is to protect the lumen of the blood vessel from injury.

The inner tube 2 is relatively slidable to the outer tube 1 and the wires fixed to the end of the inner tube are three dimensionally expanded when projecting out of the outer tube. The outer tube 1 has a projecting engaging device 7 and the grip 3 has a stopper device, and fitting them with each other certainly stops the rotation of the outer tube to secure stabilized use.

Figure 3:
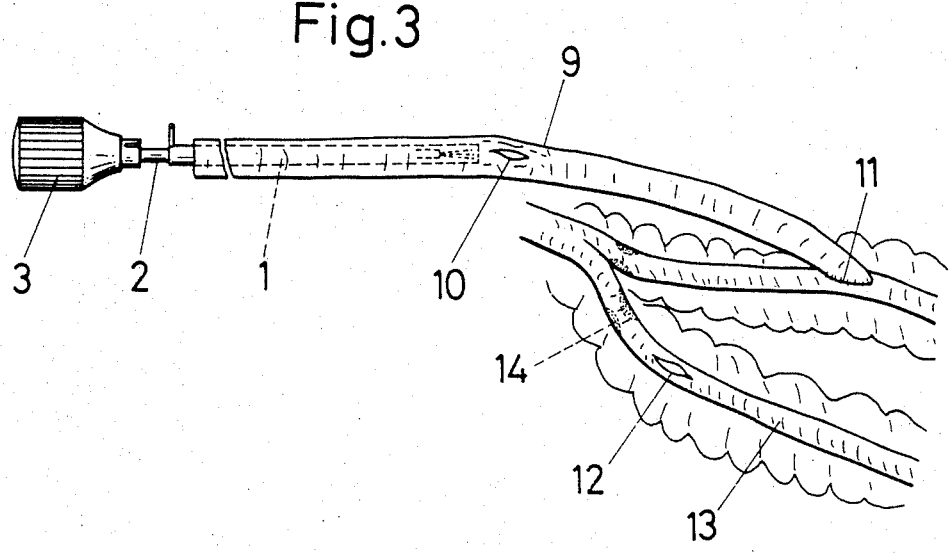
FIGS. 3 to 5 are illustrations showing an example of the usage of the incision opening expansion holder in coronary artery bypass operation.
Figure 4:
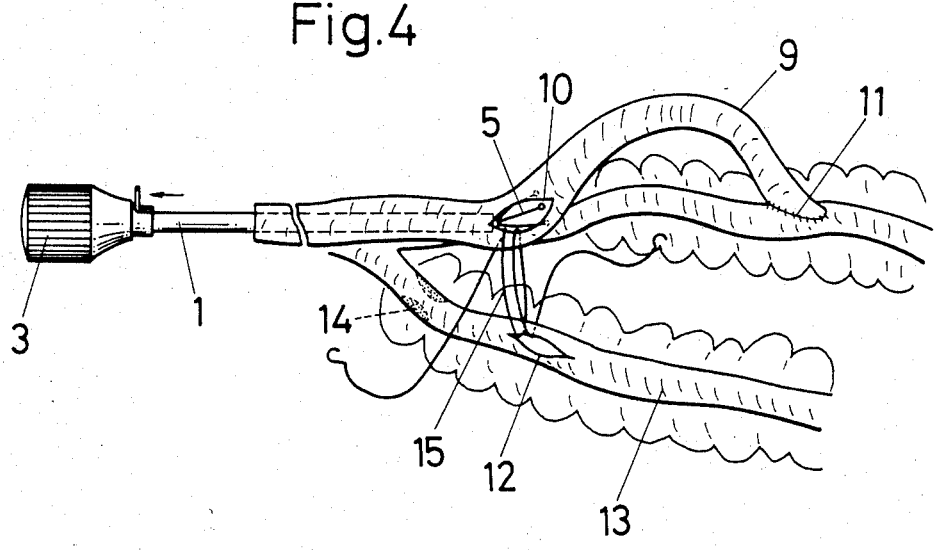
Figure 5:
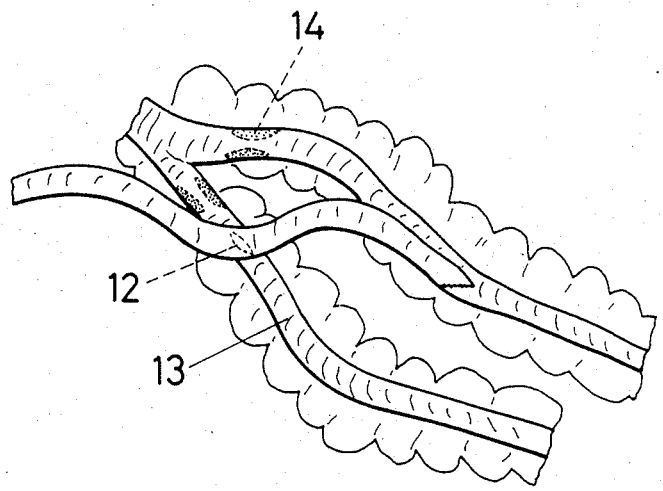

An example of use in coronary artery bypass operation is shown in FIGS. 3 to 5. 9 represents a vein graft, 10 represents an incision opening, 11 is a first inosculation, and 12 represents a second inosculated portion of side-to-side. 13 indicates the coronary artery, 14 is a thrombus, and 15 is sewing thread.

The insicion openinng expansion holder according to the invention as shown in FIG. 3 is inserted into the vein graft 9 from the cut end of the center side. Here, the inner tube 2 is in the condition the wires are accomodated in the outer tube 1. When the end of the outer tube 1 comes to the position of the incision opening 10 of the vein graft 9, the inner tube 2 is slided to put out the wires 5 from the outer tube. This will widely open the incision opening 10. Thus, the vein graft 9 is sewn both in the first inosculated portion 11 and in the second inosculated portion 12 as side-to-side inosculation, and even when thrombuses 14 have been produced in two coronary arteries 13, bypass operation is easily attained by one vein graft.

EXAMPLE 2

FIGS. 6 to 11 show another embodiment of the incision opening expansion holder according to the invention. FIG. 6 shows an outer tube 16, FIG. 7 shows an inner tube 17, and FIGS. 8 and 9 show a grip 18. They are exploded views.

The inner tube 17 is fixed at its base 19 with the setting hole 20 of the grip 18, and the inner tube 17 is covered with the outer tube 16 to complete the instrument. 21 represents short wires which are fixed with their bases to the end of the inner tube in 120 degree angle intervals. 22 represents an engaging device provided on an end of the outer tube, and 23 is a stopper device provided on the grip 18. When the engaging device 22 and the stopper device 23 fit each other as shown in FIG. 10, the wires 21 on the inner tube 17 project out of the tube 16 and are expanded three dimensionally.

The length of the outer tube 16 is 86 to 206 mm, that of the inner tube is 85 to 205 mm, and that of the wires is 10 to 25 mm. Various combinations of them are available in those ranges, providing that the wires 21 project out when the inner tube is fixed with its base 19 engaged with grip 18.

Although only preferred embodiments of the invention have been specifically illustrated and described herein, it is to be understood that minor modification could be made therein without deporting from the spirit and scope of the invention as defined in the appended claims.

What is claimed is:

1. An incision opening expansion holder for inosculation, comprising
    a cylindrical hollow elongated outer tube having a longitudinal axis;
    a cylindrical elongated inner tube having a longitudinal axis and a first end and a second end and being of a diameter smaller than the diameter of said outer tube and slidably inserted into said outer tube;
    a grip device fixed to the first end of said inner tube; and
    a plurality of resilient wires, each having one end thereof attached to the second end of said inner tube, and another end thereof having a round ball structure attached thereto, said plurality of wires being shaped to extend radially outward from said axis in a smooth curve;
    wherein said inner tube is of sufficient length to extend said second end to an end of said outer tube in an operated position and to retract the attached wires to be completely within the outer tube in a closed position; and
    wherein said wires are of sufficient resilience and axial length to be compressed into and fit completely within said outer tube in the closed position, and to extend completely outside of said outer tube in the operated position with the round ball structures located at the ends of said wires being spread out radially and with the wires being resiliently expanded to a circular shape; and
    wherein said grip device is used to move said inner tube between the operated and closed positions.

2. The holder of claims 1, wherein said grip device has an stopper device and said first end of said inner tube has an engaging device, wherein said engaging device is fit into said stopper device in said operated position with said wires being extended completely outside of said outer tube.

* * * * *